(12) United States Patent
Xiao

(10) Patent No.: US 12,246,156 B2
(45) Date of Patent: Mar. 11, 2025

(54) NEEDLE ASSEMBLY FOR LIQUID APPLICATOR

(71) Applicant: Long Xiao, North York (CA)

(72) Inventor: Long Xiao, North York (CA)

( * ) Notice: Subject to any disclaimer, the term of this patent is extended or adjusted under 35 U.S.C. 154(b) by 387 days.

(21) Appl. No.: 17/682,831

(22) Filed: Feb. 28, 2022

(65) Prior Publication Data
US 2023/0270986 A1    Aug. 31, 2023

(51) Int. Cl.
A61M 37/00    (2006.01)

(52) U.S. Cl.
CPC . A61M 37/0076 (2013.01); *A61M 2205/0216* (2013.01)

(58) Field of Classification Search
CPC .............. A61M 37/00; A61M 37/0015; A61M 37/0076; A61M 37/0084; A61M 2205/0216; A61B 11/005; A61B 5/1411; A61B 5/150412; A61B 5/15146; A61B 5/15192; A61B 17/205; A61B 17/34; A61B 17/3494; A61B 17/3496; A61B 2017/3409; A01K 11/005
See application file for complete search history.

(56) References Cited

U.S. PATENT DOCUMENTS

| | | | |
|---|---|---|---|
| 10,806,915 B2 | 10/2020 | Xiao | |
| 11,052,232 B2 | 7/2021 | Xiao | |
| 2015/0151098 A1 * | 6/2015 | Spendlove | A61M 37/00 606/186 |
| 2019/0217072 A1 | 7/2019 | Xiao | |
| 2020/0023175 A1 * | 1/2020 | Xiao | A61M 37/0084 |
| 2020/0114137 A1 * | 4/2020 | Siciliano | A61M 37/0015 |

FOREIGN PATENT DOCUMENTS

| | | | |
|---|---|---|---|
| CN | 106902452 A | 6/2017 | |
| CN | 211410687 U | 9/2020 | |
| KR | 101587235 B1 * | 1/2016 | ............ A61M 5/322 |

OTHER PUBLICATIONS

Extended European Search Report dated Aug. 11, 2023 in related European Patent Application No. 23158470.7. (8 pages).

* cited by examiner

*Primary Examiner* — Kelly J Bekker
*Assistant Examiner* — Lindsey R. Rivers

(57) ABSTRACT

A needle assembly for a liquid applicator comprises a housing, a needle bundle, and an elastic tubular member. The housing comprises a longitudinal channel having upper and lower open ends. The needle bundle is movably mounted in the channel and configured to be driven by a driving shaft to reciprocatively move between a retracted position and an extended position. The elastic tubular member comprises a first end attached to the housing and a second end attached the needle bundle to bias the needle bundle to move longitudinally towards the retracted position. The tubular member comprises a first portion and a second portion thinner than the first portion, which are separated by a boundary. The boundary extends helically between the first and second ends of the tubular member. The first portion may include one or more helical ridges.

20 Claims, 10 Drawing Sheets

NEEDLE ASSEMBLY FOR LIQUID APPLICATOR

FIELD

The present invention relates generally to devices for applying a liquid to skin, particularly to needle assembly used in liquid applicators such as tattoo devices or devices for applying permanent make-up.

BACKGROUND

Liquid applicators for applying ink to skin, such as tattoo devices, typically include a needle for applying ink to skin, a base with a needle actuator, and a needle handle that connects the needle to the base and can be conveniently held in a hand of an operator for manipulating the needle during use. In operation, the needle is actuated by the needle actuator to reciprocatively move between extended and retracted positions, thereby repeatedly puncturing the subject's skin. Tattoo needles may be provided in a needle assembly, which is often referred to as needle module and is detachably attached to the needle handle. Examples of tattoo devices include rotary tattoo machines and coil tattoo machines. Some needle modules include an elastic biasing member for sealing and biasing the needles both axially and transversally.

For example, U.S. Pat. No. 11,052,232 to Xiao, issued Jul. 6, 2021, disclosed a needle assembly with an elastic biasing member for biasing needles and forming a fluid seal.

CN106902452A by Wang, published Jun. 30, 2017, disclosed a tattoo device, which includes a shell, a needle, and an elastic membrane. A linkage structure is arranged on the needle and fixedly connects the needle with the elastic membrane. The elastic membrane has regions of different thicknesses for generate forces to move the needle backwards and towards an operation section. The elastic membrane may have an elastic rib extending along the direction of the needle movement on one side of the elastic membrane.

SUMMARY

The present disclosure relates to needle assemblies for liquid applicators. The needle assembly comprises a housing, a needle bundle, and an elastic tubular member. The housing comprises a longitudinal channel having upper and lower open ends. The needle bundle is movably mounted in the channel and configured and mounted to be driven by a driving shaft to reciprocatively move between a retracted position and an extended position. The tubular member comprises a first end attached to the housing and a second end attached the needle bundle to bias the needle bundle to move longitudinally towards the retracted position.

In a first aspect, the elastic tubular member comprises a helical ridge extending on an external surface of the tubular member such that the helical ridge provides a biasing force that biases the needle bundle both longitudinally towards the retracted position and laterally towards a lateral side of the channel of the housing.

In different embodiments, the needle assembly may include one or more of the following features. The first and second ends of the tubular member may be sealingly attached to the housing and the needle bundle to prevent fluid communication between the lower open end and the upper open end of the housing. The tubular member may comprise a diaphragm. The ridge may extend from the first end to the second end of the tubular member. The helical ridge may comprise two helical ridges arranged symmetrically with respect to a plane passing through a longitudinal axis of the tubular member. The helical ridge may comprise helically aligned step-shaped side edges. The helical ridge may comprise generally straight side edges. The helical ridge may comprise curved side edges. The helical ridge may comprise two generally parallel side edges or may comprise unparallel side edges. The helical ridge may comprise a plurality of helically arranged separate ridge sections. The helical ridge may have a generally polygonal or semi-circular cross-section. The polygonal cross-section may be triangular, rectangular, or trapezoidal. The tubular member comprises silicone, latex, or rubber.

In another aspect, the needle assembly comprises a first portion and a second portion thinner than the first portion, which portions are separated by a boundary therebetween. The boundary between the first and second portions extends helically between the first and second ends of the tubular member. As a result, the tubular member when stretched exerts a biasing force on the needle bundle that biases the needle bundle both longitudinally towards the retracted position and laterally towards a lateral side of the channel in the housing.

In different embodiments, the needle assembly may include one or more of the following features. The first and second ends of the tubular member may be sealingly attached to the housing and the needle bundle to prevent fluid communication between the lower open end and the upper open end of the housing. The first and second portions of the tubular member may be separated by two helical boundaries, arranged symmetrically with respect to a plane passing through a longitudinal axis of the tubular member. The second portion of the tubular member may comprise a bellows section. The first and second portions of the tubular member may be separated by a helically aligned step-shaped side wall or a curved side wall at the boundary. The tubular member may comprise silicone, latex, or rubber.

As can be appreciated, the helical profile of the ridge or boundary on the tubular member provides a biasing force that has both a longitudinal component and a lateral component.

Other aspects, features, and embodiments of the present disclosure will become apparent to those of ordinary skill in the art upon review of the following description of specific embodiments in conjunction with the accompanying figures.

BRIEF DESCRIPTION OF THE DRAWINGS

In the figures, which illustrate, by way of example only, embodiments of the present disclosure.

DETAILED DESCRIPTION

An embodiment of the present disclosure relates to needle assemblies for use in liquid applicators for applying a liquid to skin.

The liquid applicator may be an ink applicator, such as tattoo devices as described in U.S. Pat. Nos. 11,052,232; 10,806,915; or US 20190217072, the entire contents of each of which are incorporated herein by reference. Briefly, a suitable tattoo device (not shown) may include a needle module coupled by a needle handle (not shown) to a base device (not shown). The needle module may be a disposable needle module. The needle module and the needle handle may be configured to be removably coupled to each other.

In an embodiment disclosed herein, the needle assembly may be a needle module 10 as illustrated in FIGS. 1 to 8B. The needle module 10 may be configured to apply tattoo or permanent make-up to skin. The needle module 10 may be a disposable module.

Figure 1:
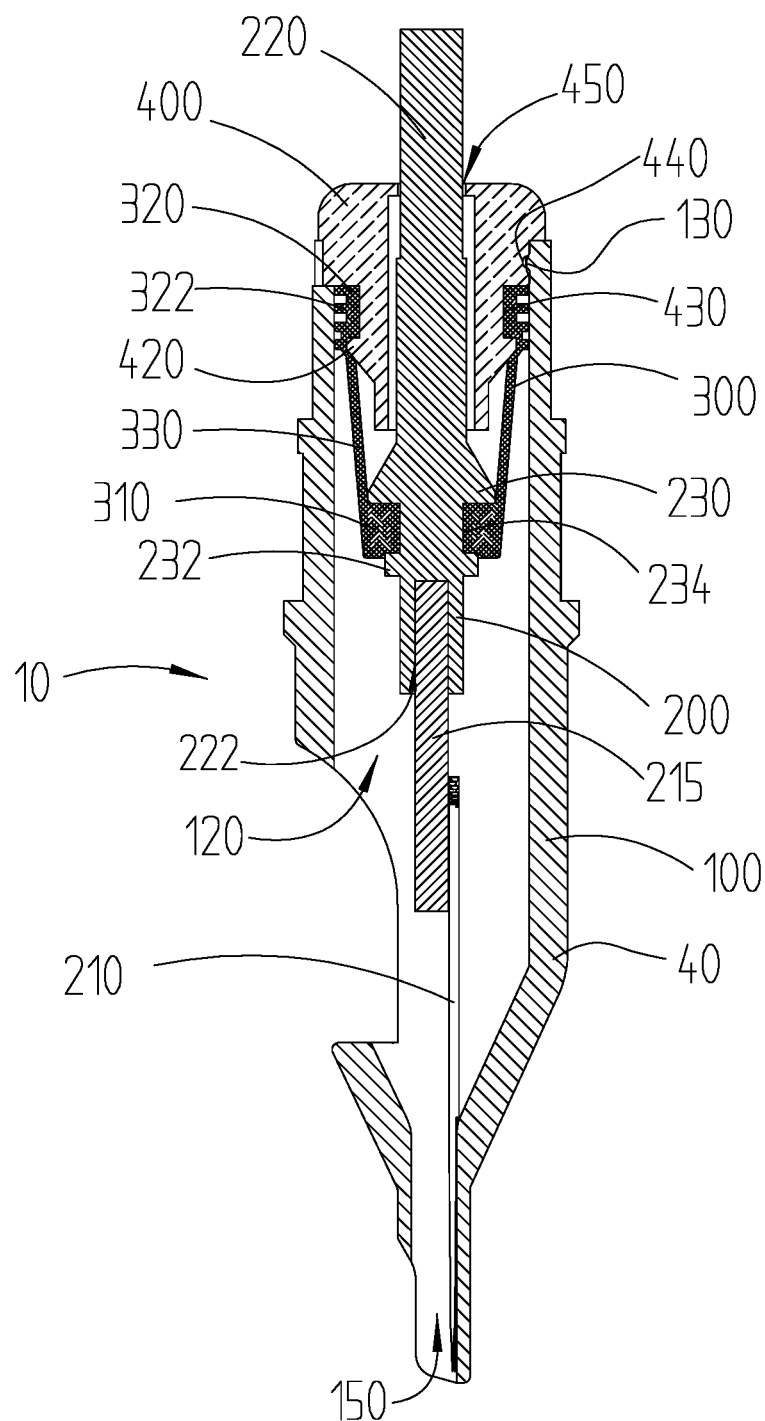
FIG. 1 is a cross-sectional view of a needle assembly, illustrative of an embodiment of the present disclosure.

As illustrated in FIG. 1, needle module 10 includes housing 40 and a reciprocatively movable needle bundle 200 with a needle tip portion 210 mounted in the housing 40 for applying ink to the skin of a subject.

While not shown in the drawings, it should be understood that the needle module 10 can be attached or connected to a tattoo machine (not shown), such as through a handle (not shown) of the tattoo machine. A base device (not shown) of the tattoo device includes a needle actuator (not shown) with a drive shaft (not shown) for actuating downward movement of the needle bundle 200 through a needle shaft portion 220 of the needle module 10.

The construction and operation of a suitable tattoo machine, including its handle and base device, are known in the art, and can be similar to, for example, the corresponding devices and parts disclosed in U.S. Pat. Nos. 11,052,232, 10,806,915, or US 20190217072. As such, these devices, parts, and their operation, and their coupling and interaction with housing 40 and needle shaft portion 220 are not described in detail herein.

As depicted in FIGS. 1-5B, the needle bundle 200 is movably mounted in needle housing 40. The needle housing 40 includes a tubular body portion 100 and a removable cap 400.

Figure 4:
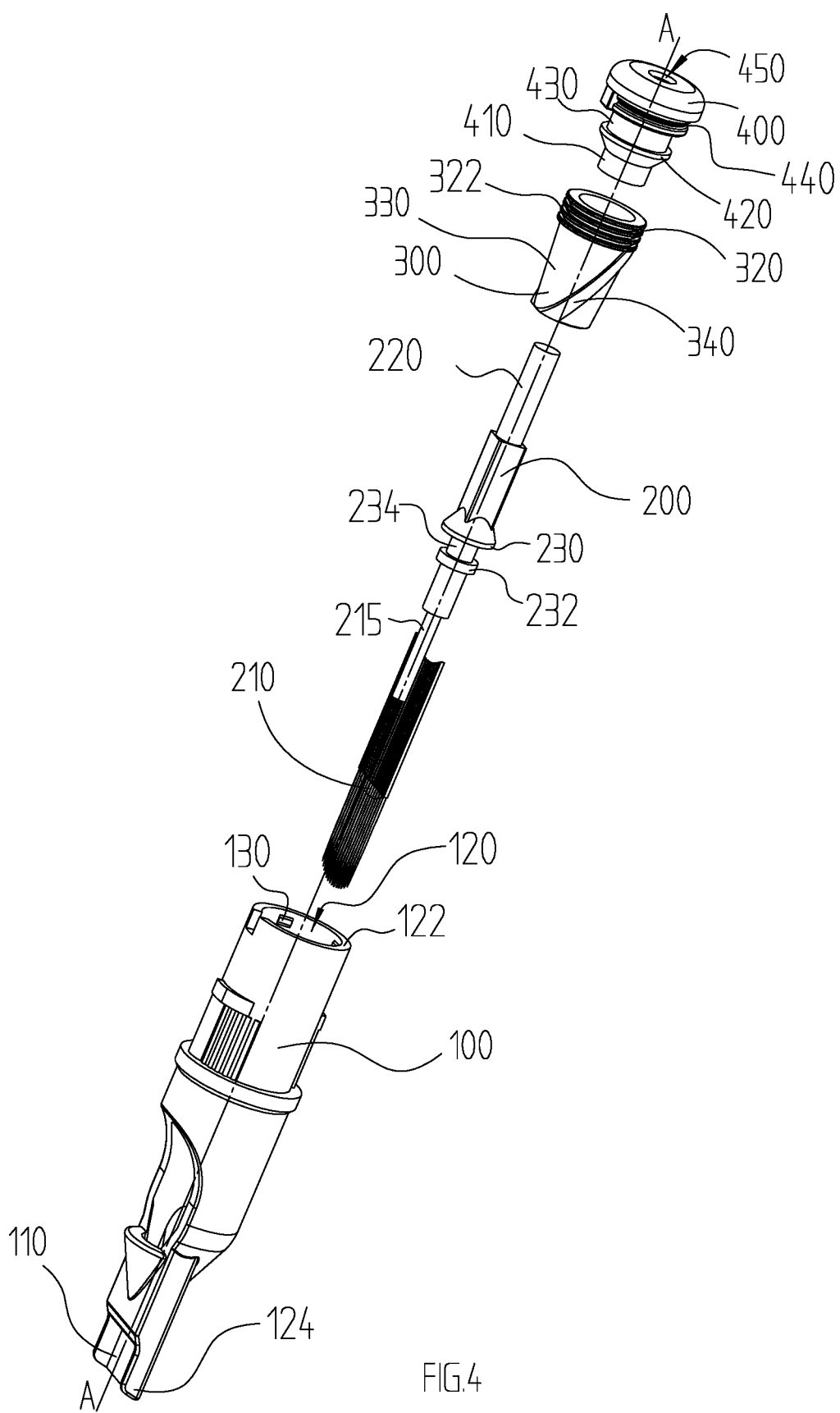

The body portion 100 has a tubular longitudinal inner channel 120 for receiving and housing the needle bundle 200. The channel 120 extends from an upper open end 122 to a lower open end 124 of the body portion 100, and has a central longitudinal axis (A), as shown in FIG. 4 (also see FIG. 5A). The body portion 100 has an opening 150 at the lower open end 124 to allow the needle tip portion 210 of the needle bundle 200 to pass through. A needle guiding wall 110 is provided at the lower open end 124 adjacent the opening 150, which provides a guide surface for guiding movement of the needle Up portion 210.

The opening 150 may be provided as an integral part of the body portion 100 as depicted in the drawings. However, in other embodiments, the opening 150 may be provided in a separate mouthpiece (not shown) attached to the body portion 100. The mouthpiece can be constructed and provided according to known techniques, including those disclosed in the references incorporated herein.

The body portion 100 may also have one or more internal coupling ribs 130 at the upper open end 122 for coupling with and engaging the cap 400, as will be further described below.

The removable cap 400 is provided at and coupled to the upper open end 122 of the tubular body portion 100. The cap 400 has a central opening 450 for allowing the needle shaft portion 220 to pass therethrough and axially move up and down during operation. Cap 400 also has a downward extending tube 410, with an external annular rim 420 and a lower external annular groove 430, which are provided and configured for engaging an upper end portion 320 of the tubular member 300 to affix the upper end portion 320 to the housing 40, as will be further described below. The cap 400 also has an upper annular groove 440 for engaging coupling ribs 130 of the body portion 100, so as to secure the cap 400 in position.

Each or both of body portion 100 and cap 400 may be made of a plastic material, or any other suitable material.

As already alluded to above and illustrated in FIGS. 1-5, the needle bundle 200 has a needle tip portion 210 attached to a needle shaft portion 220.

In various embodiments, the needle tip portion 210 of the needle bundle 200 may include one or more needle tips, which may be welded together, or otherwise bounded together. The needle tips may be formed of stainless steel or any other suitable material. The individual needle tip may have any suitable or known needle tip shape. The needle tips may be arranged to form a tip portion that has a generally or substantially cylindrical or conical profile. Alternatively, the needle tips may be arranged side-by-side to form a tip portion that has a generally flattened or band-shaped profile. Rows of side-by-side needles may also be stacked. Such different arrangements of tattoo needles are known in the art and may be referred to as "Round Liner" needles, "Round Shader" needles, "Flat" Needles, or "Magnum" needles, respectively. Needle tip portion 210 may include 1-18 individual needle tips for "Round Liner" needles and "Round Shader" needles, or may include 4-27 needle tips for "Flat" needles and "Magnum" needles.

As can be appreciated, the cross-sectional sizes or diameters of the needles or needle bundles will affect how the ink will flow. Typically, the smaller the needle tip size or narrower the diameter of the needle tip, the finer and more controlled the stream of ink that flows off each needle tip. Typically, the needle tips in the same needle bundle may be of the same or similar sizes. The size of the needle tips may be selected based on the desired effects by the operator or user. Different sizes may be used for different reasons. Standard sizes of needles may be used. The diameters of the individual needles may be 0.25 mm, 0.30 mm, or 0.35 mm in some embodiments. The designs of the needle tips may be selected and vary as known in the art based on the desired tattooing techniques and purposes to be applied.

The number of needles in a needle bundle 200 may vary from 1 to 27 or more as desired. For example, commercially available round needle bundles typically have 1, 3, 5, 7, 8, 9, 11, 14, or 18 needles in each bundle. It can also be appreciated that the overall profile of the needle bundle may change and vary depending on the number of needles in the bundle, their arrangement, the amount of soldering material used, or other factors.

The needle tips in needle tip portion 210 are supported on needle shaft portion 220. The axis of needle shaft portion 220 may be axially aligned with the axis of channel 120 (axis A shown in FIG. 4 and FIG. 5A), but is off-set from the axis of the needle tip portion 210 (see FIGS. 3, 4 and 5A). The needle shaft portion 220 may be formed of a rigid plastic material or another suitable material. The material in needle shaft portion 220 should have relatively high strength and high hardness and be wear-resistant so that its sufficiently rigid and strong to support stable movement of the needle tip portion 210 during operation.

In the embodiment as depicted in FIG. 1, the needle tip portion 210 is attached to needle shaft portion 220 through an optional connection rod 215 of the needle bundle 200. Connection rod 215 may be made of steel such as stainless steel. An end of the connection rod 215 may be attached by an adhesive to needle shaft portion 220 in a bore 222 in the needle shaft portion 220. The needle tip portion 210 may be attached to the other end of the connection rod 215 such as by soldering. The connection rod 215 may have a diameter of about 1.5 mm, and the bore 222 in the needle shaft portion 220 may have a corresponding diameter.

In an alternative embodiment, the needle tip portion 210 may have a cylindrical end which is directly inserted into the bore 222 of the needle shaft portion 220 for attachment to the needle shaft portion 220 such as by an adhesive. However, when the needle tip portion 210 is attached to the needle shaft portion 220 through the connection rod 215, the needle tip portion 210 may have different sizes or different number of needles, and it is not necessary for the needle tip portion 210 to have a cylindrical end with the shape and size that match the shape and size of the bore 222.

Figure 5A:
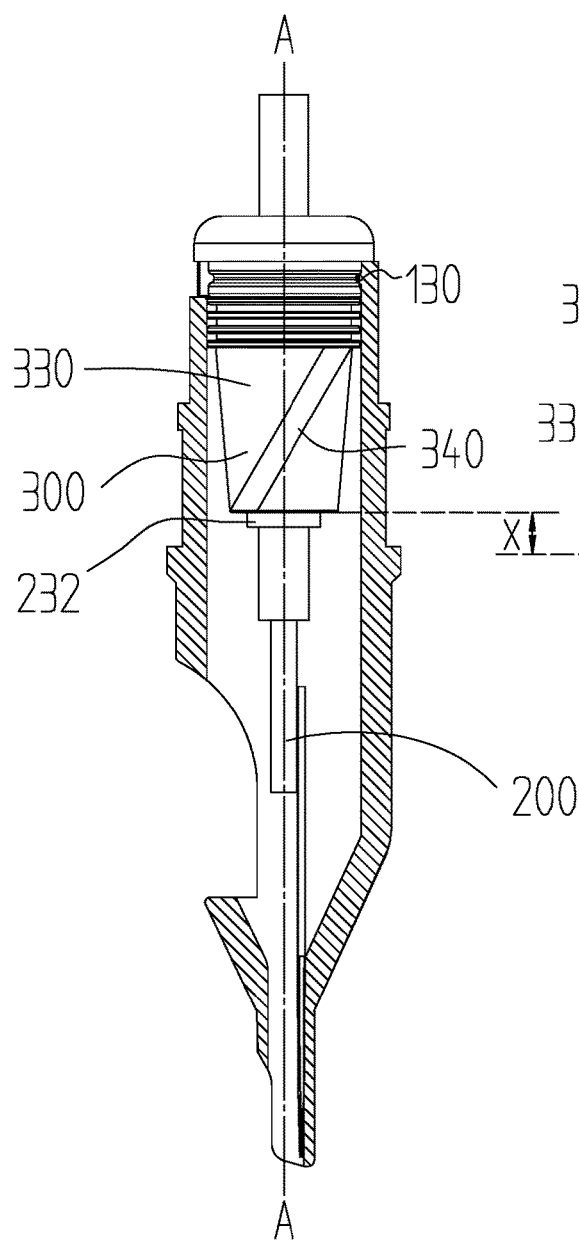
FIGS. 5A and 5B are partially cross-sectional and partially elevation views of the needle assembly of FIG. 1, with the needle bundle in the retracted position (5A) or the extended position (5B) respectively.
Figure 5B:
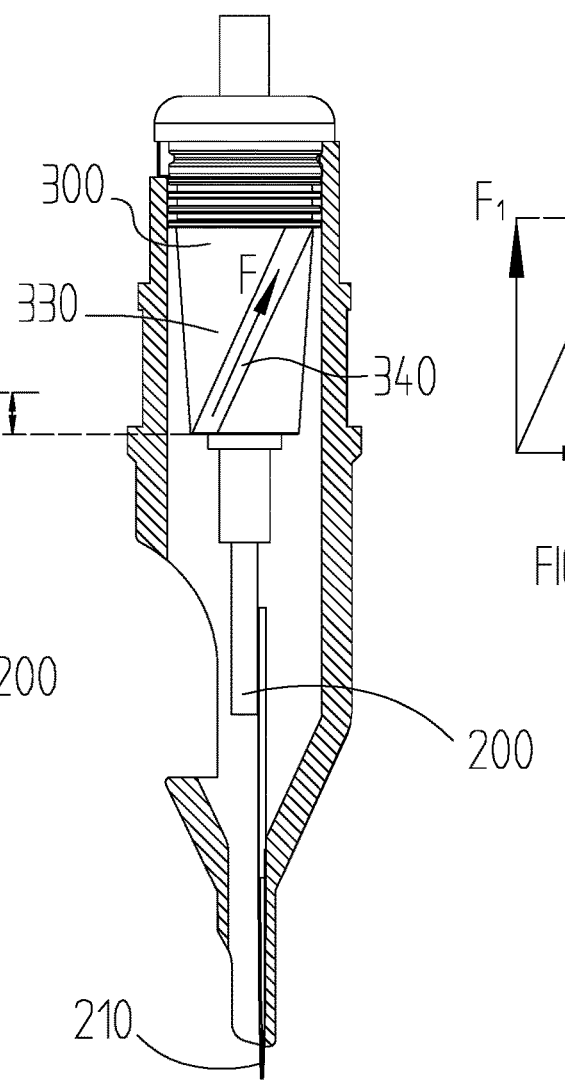

Needle bundle 200 may reciprocally move longitudinally along axis A between the retracted position, illustrated in FIG. 5A, and the extended position, illustrated in FIG. 5B. As noted, the downward movement of needle bundle 200 is actuated by the actuator of the tattoo machine to which the needle bundle 200 is connected.

To facilitate the reciprocal movement of the needle bundle 200, an elastic tubular member 300 is provided within housing 40 and configured to pull the needle bundle 200 upward during each stroke cycle after the needle bundle 200 has been pushed down by an actuating or driving mechanism such as the drive shaft of the tattoo device described above.

The tubular member 300 is also configured to bias the needle tip portion 210 of the needle bundle 200 laterally towards a lateral side of the channel 120, such as the needle guiding wall 110.

Furthermore, tubular member 300 is configured and assembled to provide a fluid seal between the lower open end 124 and the opening 450 of the cap 400 in the housing 40. The tubular member 300 may thus form a fluid seal between the lower open end 124 and the opening 450.

Conveniently, when a fluid, such as ink or blood or other bodily fluid, enters housing 40 through opening 150, the seal provided by tubular member 300 will prevent the fluid from passing through opening 450 and from contaminating the upper components in the housing 40 including the upper section of the needle shaft portion 220 that will extend to outside the opening 450 during operation. Consequently, the fluid is contained within housing 40 and contamination of components of the tattoo device connected to the needle module 10 can be prevented. The fluid in the housing 40 may be disposed with the needle module 10 when the needle module 10 is discarded after use. For a new subject to be tattooed, a new needle module 10 may be used and connected to the tattoo device to prevent cross-contamination through the needle module.

As can be better seen in FIGS. 7B-7D and 8A, the tubular member 300 includes a lower end portion 310, an upper end portion 320, and a middle, tubular section 330 connecting the upper end portion 320 and lower end portion 310.

The upper end portion 320 of tubular member 300 is sized and shaped to close fit with the inner wall of tubular body portion 100. The upper end portion 320 has annular ridges extending along the circumference of the outer wall of upper end portion 320, which provide fluid sealing and frictional fitting with the inner wall of tubular body portion 100.

As noted earlier, cap 400 is configured to engage the upper end portion 320 of tubular member 300. In particular, the upper end portion 320 is securely retained between cap 400 and tubular body portion 100 in annular groove 430 by annular rim 420, and is thus sealingly affixed to housing 40.

Figure 8A:
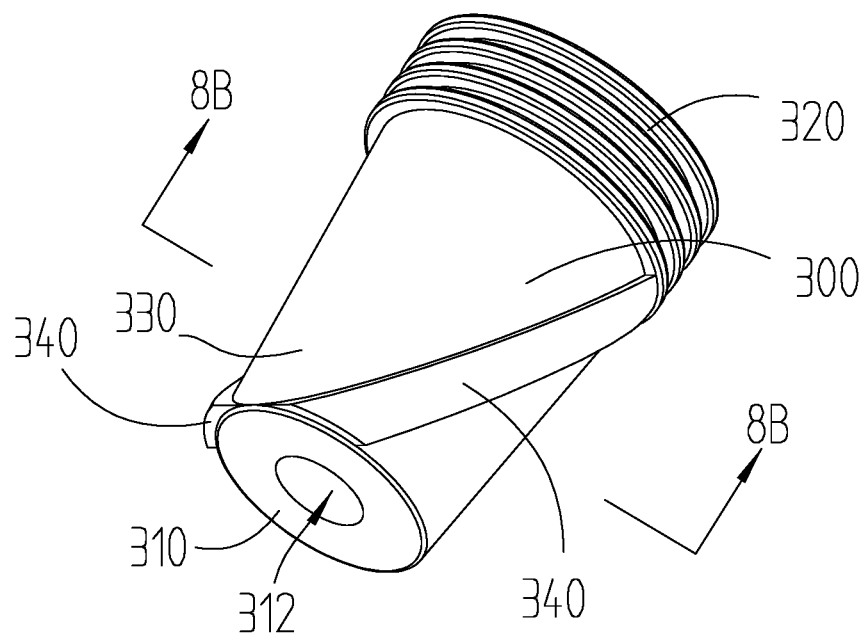
FIG. 8A is a bottom perspective view of the tubular member of FIG. 7A.
Figure 8B:
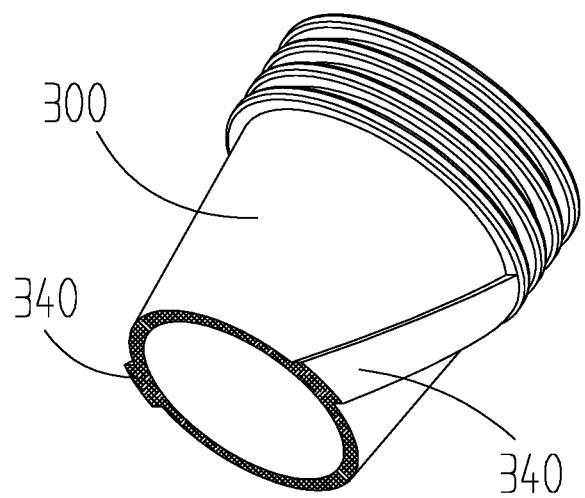
FIG. 8B is a perspective view of a cut-off portion of the tubular member of FIG. 7A, which is cut along line 8B-8B in FIG. 8A.

The lower end portion 310 of tubular member 300 is configured to sealingly engage the needle shaft portion 220 of needle bundle 200. As depicted in FIG. 8A, the lower end portion 310 of tubular member 300 may include a central opening 312 for allowing the needle shaft portion 220 to pass through and frictionally engaging the needle shaft portion 220 with fluid sealing.

The middle tubular section 330 has a tubular shape and includes a helical ridge 340, or wall sections of different thickness separated by a helical boundary, as will be further described below.

Notably, the tubular member 300 in embodiments described herein and shown in the drawings is constructed differently from the biasing member disclosed in U.S. Pat. No. 11,052,232 or the biasing member disclosed in US 20190217072.

Figure 3:
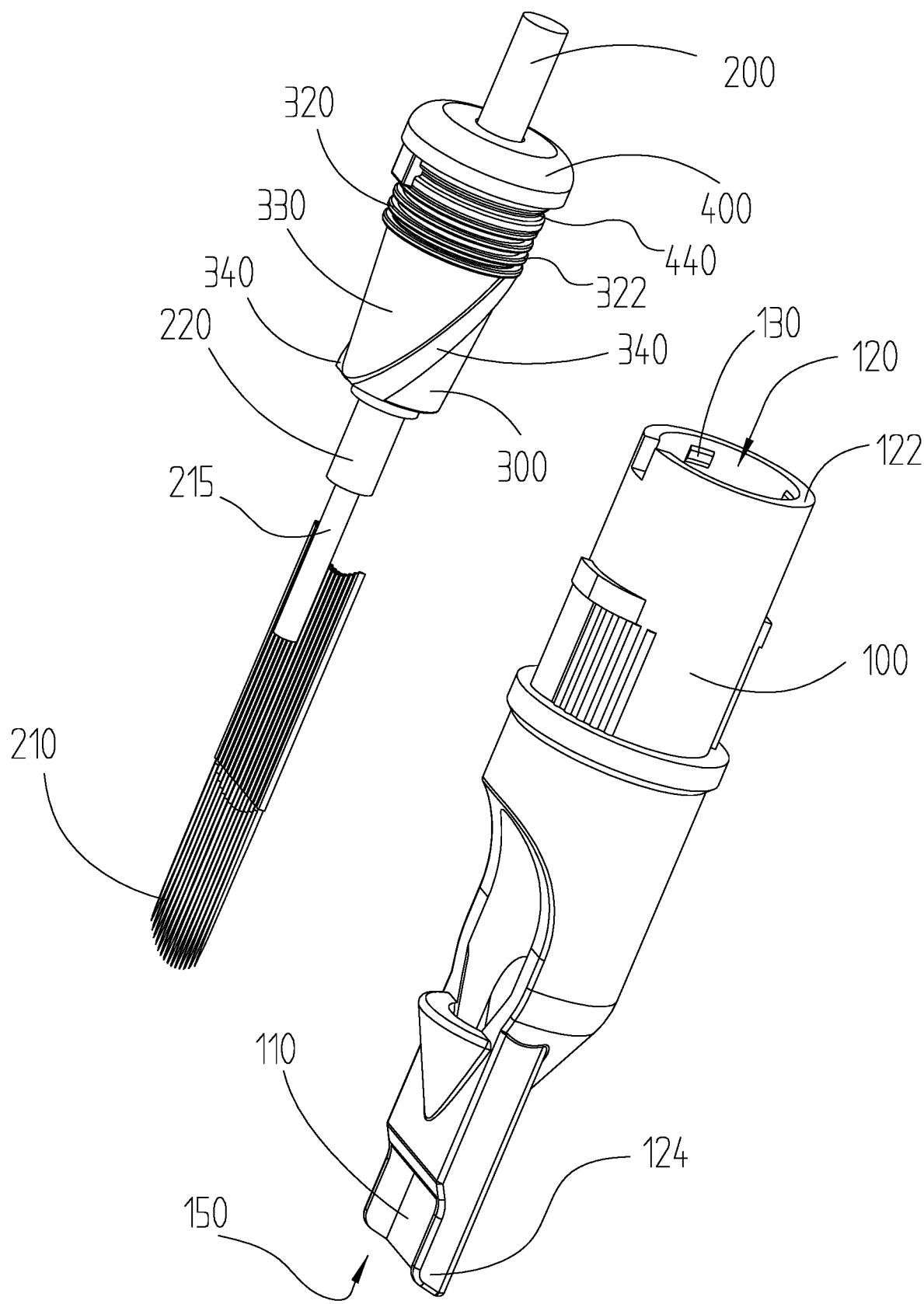
FIGS. 3 and 4 are exploded perspective views of the needle assembly of FIG. 2.

Specifically, as depicted in FIGS. 3-5 and in FIGS. 5A-8B, the tubular member 300 in the illustrated embodiment includes two helical ridges 340 extending on its external surface. The two helical ridges 340 are symmetrically positioned with respective to a plane passing through the central longitudinal axis of the tubular member 300, which is aligned with axis A as shown in FIGS. 4 and 5A. As shown in FIG. 7B, the symmetry plane is indicated by line B-B, and will be referred to as symmetry plane B hereinafter. Conveniently, the helical ridges 340 provide biasing forces that bias the needle bundle 200 laterally toward a lateral side of the channel 120 in addition to biasing the needle bundle 200 longitudinally upwards.

As used herein, a "helical ridge" refers to a ridge that extends along a cylindrical external surface in both the axial or longitudinal direction and the circumferential direction. The three-dimensional (3D) profile of the ridge may form a generally geometrical helix or spiral. However, in different embodiments, a helical ridge may have other curved or straight-edged shapes that do not form a perfect helix or spiral. For example, a helical ridge may have a shape similar to that of the slanted tooth trace on a helical gear. A "helical boundary" also refers to a boundary line that extends along a cylindrical external surface in both the axial or longitudinal direction and the circumferential direction. As used herein, a "helical" line refers to a line that extends in three dimensions and is not parallel to any straight line nor within any single plane.

The first and second ends of the tubular member are sealingly attached to the housing and the needle bundle, to prevent fluid communication between the lower open end and the upper open end of the housing. Thus, the tubular member 300 also functions as a seal. The tubular member 300 may comprise a diaphragm for this purpose.

In the embodiment depicted in FIGS. 1-8B, the helical ridges 340 extend from the first end to the second end of the tubular member 300. However, in different embodiments, one or more shorter helical ridges, or a plurality separate ridge sections arranged in a helical pattern, may be provided on tubular member 300 to provide the lateral biasing force.

Figure 7A:
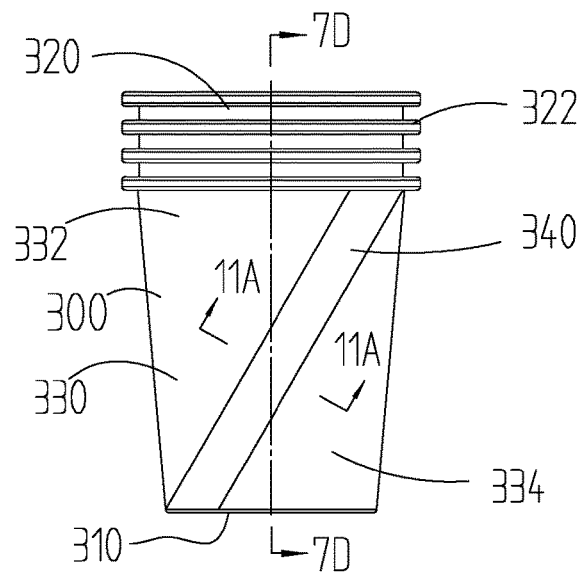
FIG. 7A is a front elevation view of a tubular member, according to an embodiment of the present disclosure.

As depicted in FIGS. 5A, 5B, and 7A, the helical ridges 340 comprise generally straight side edges when viewed in a side elevation view. However, in different embodiments, the side edges of the helical ridges 340 may have different shapes or profiles, as will be described in more detail below.

The tubular member 300 may also be considered to include thicker portions and thinner portions, and the thicker and thinner portions are separated by a helical boundary therebetween that extends helically between the first end and the second end of the tubular member 300. For example, in various embodiments of the tubular member 300 as shown in FIGS. 5A-8B and 9A to 9D, the helical ridges 340 are thicker portions and the regions between the helical ridges 340 are the thinner portions, and the boundaries are at the bottom edges of the helical ridges 340.

Figure 9A:
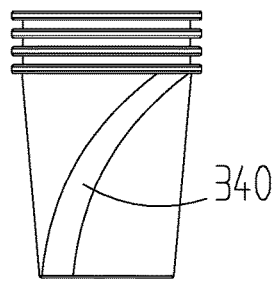
FIGS. 9A-9G are elevation views of different tubular members, according to different embodiments of the present disclosure.
Figure 9B:
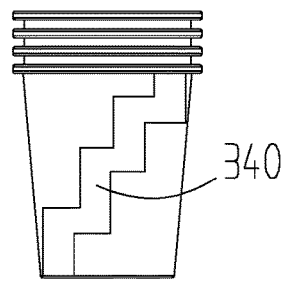
Figure 9C:
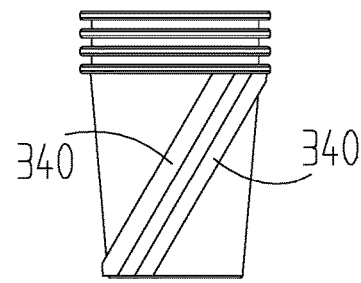
Figure 9D:
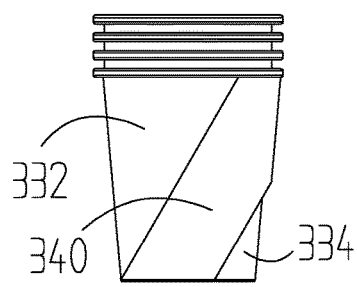
Figure 9E:
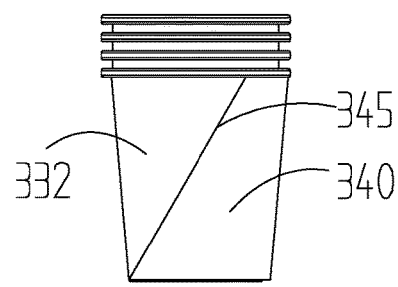

In some embodiments, a tubular member 300 may comprise only two portions, one thicker portion and one thinner portion as illustrated in FIG. 9E. The two portions are separated by two helical boundaries 345, which may be arranged symmetrically with respect to a plane passing through a longitudinal axis of the tubular member 300. A curved side wall may be formed at the helical boundary between the thinner and thicker portions.

The thinner portion of the tubular member 300 may comprise one or more bellows sections. The tubular member 300 may be provided with one bellows section on one side of the tubular member 300, such as at the wall 332 as illustrated in FIG. 9H, or with two bellows sections on opposite sides, such as at both the wall 332 and the opposite wall 334 as illustrated in FIG. 9I.

Tubular member 300 may be formed of a silicone material or another resilient material such as latex, rubber, or an elastomer. The resilient material may be selected such that it is sufficiently elastic to be extended under stress to the desired extended position to expose the needle tips, but also sufficiently resilient to provide the required biasing force for returning the needle bundle 200 from the extended position back to the retracted position. In one embodiment, tubular member 300 may be formed from a silicone material with a Shore hardness from about 30 A to about 50 A.

During use, the needle module 10 is attached to a handle of a tattoo device and the needle bundle 200 is driven by a needle actuator of the tattoo device to move downward so that the needle bundle 200 will move to the extended position in which the needle tips extend to outside of the lower opening 150 of the housing 40. The tubular member 300 conveniently facilitates reciprocal movement of the needle bundle 200 by pulling the needle bundle 200 upwards during each movement cycle after the needle bundle 200 has been pushed downward by the actuator. The biasing force is increased as the elastic tubular member 300 is stretched further and further during the downward movement of the needle bundle 200.

Further, due to the helical profile of the helical ridge 340 (or the helical boundary), the tubular member 300 also biases the needle tip portion 210 of the needle bundle 200 towards one side of the housing channel 120, such as towards the guiding wall 110 at the lower end near the opening 150. This lateral biasing of the needle tip portion 210 towards or against the guiding wall 110 can stabilize the needle bundle and maintain steady contact between the needle bundle 200 and the guiding wall 110.

In addition, tubular member 300 conveniently provides a fluid seal between the lower open end 150 and the upper open end 450 of the housing 40.

The upper end portion 320 of tubular member 300 is configured to engage the inner wall of body portion 100 and cap 400. For example, as best depicted in FIG. 7A, the upper end portion 320 of the tubular member 300 may include a number of annual ridges 322, which are sized and shaped to close fit with the inner wall of the tubular body portion 100. In the depicted example, the upper end portion 320 has 4 annular ridges extending along the circumference of the outer wall of the upper end portion 320. The inner wall of upper end portion 320 defines an opening that allows the needle shaft portion 220 of the needle bundle 200 to pass through and for engaging the cap 400.

After assembly, the upper end portion 320 is securely retained between cap 400 and tubular body portion 100 and is sealingly affixed to housing 40. As the upper end portion 320 of tubular member 300 is not attached to needle bundle 200, it does not move when the needle bundle 200 moves up and down. Thus, during operation the upper end portion 320 of tubular member 300 is fixed in position relative to the housing 40.

The lower end portion 310 of tubular member 300 is configured to sealingly engage the needle shaft portion 220 of needle bundle 200. The lower end portion 310 has an opening 312, which is sized and shaped such that the needle shaft portion 220 forms a close fit with the lower end portion 310 at the opening 312, so as to form a fluid-tight seal between the tubular member 300 and the needle bundle 200, while at the same time allowing the shaft portion 220 to axially move up and down during operation without breaking the seal.

For example, as can be better seen in FIGS. 1 and 7O, the lower end portion 310 has a thickened section with an upward facing surface, and the needle shaft portion 220 may have an enlarged section, shoulder 230, that engages the upward facing surface of the lower end portion 310 of the tubular member 300. The thickened section of the lower end portion 310 is sized and shaped to closely couple with the shoulder 230, such that shoulder 230 exerts a downward force on the thickened section of the lower end portion 310 to pull the lower end portion 310 down when the needle bundle 200 is driven by the needle actuator to move towards the extended position. As the lower end portion 310 is pulled downward, the tubular member 300 is stretched and the length of the tubular member 300 increases. As a result, the tubular member 300 produces a biasing force to bias the needle bundle 200 upward. After the needle actuator stops driving the needle bundle 200 downward and the needle bundle 200 reaches the final extended position, the biasing force applied by the tubular member 300 pulls the needle bundle 200 back up to the retracted position.

To further limit the relative movement between the lower end portion 310 of tubular member 300 and the needle bundle 200, the needle bundle 200 may optionally include a collar 232 spaced from the shoulder 230 by a neck section 234 therebetween, so that the lower end portion 310 of the tubular member 300 can be received in the groove formed by the shoulder 230, collar 232 and neck section 234 to attach the lower end portion 310 to the needle bundle 200. Thus, the movement of the lower end portion 310 relative to the needle bundle 200 is limited and restricted by shoulder 230 and collar 232.

In different embodiments, the tubular member 300 may be formed of an elastic and resilient material, which may be selected such that it is sufficiently elastic to be extended under stress to the desired extended position to expose the needle tips, but also sufficiently resilient to provide the required biasing force for returning the needle bundle 200 from the extended position back to the retracted position, and for applying an adequate lateral biasing force to press the needle tip portion 210 of the needle bundle to a selected side of the channel in the housing 40, such as the guiding wall 110 as illustrated in FIG. 3. In some embodiments, the resilient material may be a silicone material with a Shore hardness from about 25 A to about 50 A.

In the embodiment depicted in the drawings, the upper end portion 320 and lower end portion 310 each has a wall thickness that is greater than the wall thickness of the middle tubular section 330. The upper end portion 320 and lower end portion 310 may be more rigid, less elastic, and less resilient, than the middle tubular section 330.

FIGS. 5A and 5B show the needle module 10 with the needle bundle 200 in the retracted (FIG. 5A) and extended (FIG. 5B) positions respectively. As can be seen in FIG. 5A, even in the retracted position, tubular member 300 may still be slightly stretched and exert a biasing force to press the needle shaft portion 220 so that the needle tip portion 210 of the needle bundle 200 is pushed towards or against a side wall of the housing 40.

Figure 6:
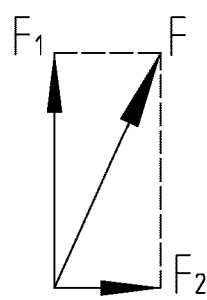
FIG. 6 is force diagram showing the biasing force and its longitudinal and lateral component applied by the tubular member in the needle assembly of FIG. 5B.

As shown in FIG. 5B, the middle tubular section 330 of the tubular member 300 is further stretched and tensioned at the extended position by a length X, and thus produces a relatively large biasing force. Conveniently, the helical ridge 340 when stretched produces a biasing force $\vec{F}$, generally directed along the helical direction of the helical ridge 340, as illustrated in FIG. 5B. The biasing force $\vec{F}$ has a longitudinal component $\vec{F}_1$ in the axial direction A of channel 120 and the needle shaft portion 220, and a lateral component $\vec{F}_2$ in a lateral direction generally perpendicular to the axial direction A, where $\vec{F}=\vec{F}_1+\vec{F}_2$, as illustrated in FIG. 6. The longitudinal component $\vec{F}_1$ pulls the needle bundle 200 upward towards the retracted position, and the lateral component $\vec{F}_2$ presses the tip end of the needle bundle 200 towards the guiding wall 110.

For a typical tattoo machine, the distance X between the retracted and extended positions of needle bundle 200 may be about 2 mm to about 5 mm, as the driving shaft of the needle actuator in a typical tattoo machine can move the same distance during each stroke.

As can be appreciated, in the retracted position as shown in FIG. 5A, the tubular member 300 may still be tensioned. For example, when the needle module 10 is not connected to the handle of a tattoo machine (not shown), the tubular member 300 may be tension free and in a relaxed state. However, when housing 40 of the needle module 10 is coupled to or connected to the handle of the tattoo machine, the needle shaft portion 220 may be initially pushed downward such as by about 2 mm to about 4 mm relative to the housing body portion 100. This downward movement of the needle shaft portion 220 tensions the tubular member 300 even though the needle bundle 200 is still in the retracted position initially. During use, the needle shaft portion 220 and needle bundle 200 may be pushed to move further downward by about 2 mm to about 5 mm.

As discussed earlier, the annular rim 420 and groove 430 of cap 400 engages the upper end portion 320 of tubular member 300, and upper end portion 320 is secured in position between the cap 400 and the inner wall at the upper end of channel 120, so that upper end portion 320 cannot move relative to the housing body portion 100 in the longitudinal direction (along axis A) during operation while the needle bundle 200 reciprocally moves up and down relative to the body portion 100. The upper end portion 320 of tubular member 300 is also configured to abut and resiliently grip the inner wall of the housing body portion 100 and to provide a tight seal between the upper end portion 320 and the housing body portion 100.

As better illustrated in FIGS. 7B, 7C, 8A, and 8B, two symmetrically arranged helical ridges 340 may be provided. Each ridge may be rib-shaped.

Figure 2:
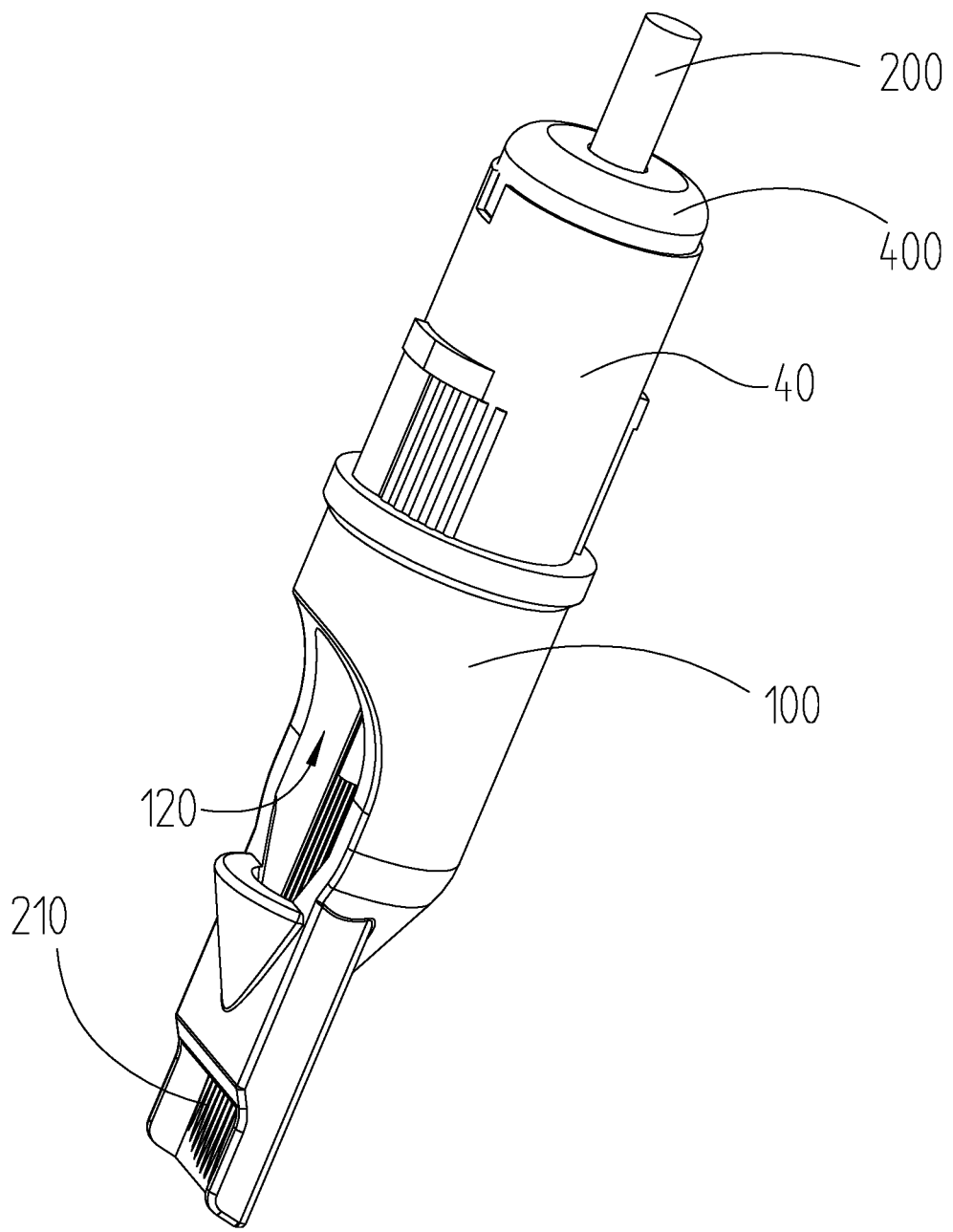
FIG. 2 is a perspective view of the needle assembly of FIG. 1.
Figure 7B:
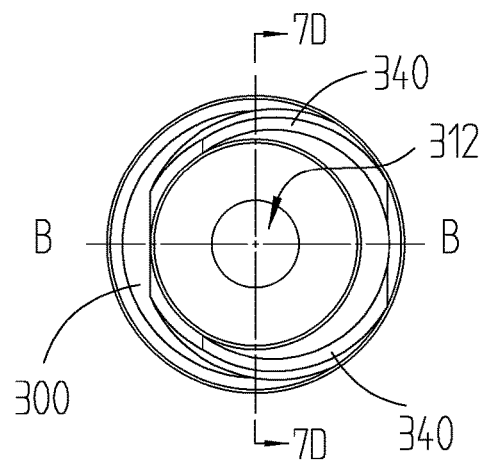
FIG. 7B is a bottom view of the tubular member of FIG. 7A, showing the symmetry plane indicated by line B-B.

The lower opening 150 in housing 40 may have different shapes and sizes. For example, if the needle bundle 200 in the needle module 10 is a flat needle bundle with a row of needles as illustrated in FIGS. 2, 3 and 4, the opening 150 may have a corresponding rectangular profile. Further, the needle guiding wall 110 may have a corresponding flat inner surface, also as illustrated in FIGS. 3 and 4. In the embodiment as depicted in FIG. 7B, the symmetrical plane B passes through and is parallel to the central axis A and is perpendicular to the guiding wall 110 of the housing body portion 100. Two helical ridges 340 are arranged symmetrically with respect to the symmetrical plane B.

In different embodiments, the needle tip portion 210 of the needle bundle 200 may have a generally cylindrical overall profile, in which case the opening 150 of the housing 40 may be circular. The inner wall of the guiding wall 110 may also be curved. The needle bundle 200 may contact the guiding wall 110 along a longitudinal line, which is referred to the needle guiding line herein. In this case, the symmetrical plane B may contain both the axis A and the needle guiding line.

As noted earlier, in different embodiments, the helical ridges 340 on tubular member 300 may have different shapes and configurations.

For example, in some embodiments, as shown in FIG. 9A, a helical ridge 340 may have curved side edges when viewed in the side elevation view. In other words, the edges of the helical ridge 340 in some embodiments may be curved in the face-on elevation view, when the viewer is directly facing the helical ridge 340.

In some embodiments, a helical ridge 340 may have generally parallel side edges as shown in FIG. 7A or may have unparallel side edges as shown in FIG. 9A.

In some embodiments, as shown in FIG. 9B, a helical ridge 340 may have helically aligned step-shaped side edges. That is, the edges of the helical ridge 340 in some embodiments may be step-shaped or zig-zap shaped in the face-on elevation view.

Two or more helical ridges 340 may also be arranged side-by-side, and generally parallel to one another, as illustrated in FIG. 9C. The two or more helical ridges 340 may be positioned on one side of the tubular member 300.

As illustrated in FIGS. 7A and 9D, the helical ridges 340 may have different widths in different embodiments. The helical ridges 340 may also have different heights in different embodiments. As can be appreciated, a wider or taller ridge may provide a larger biasing force.

Figure 9F:
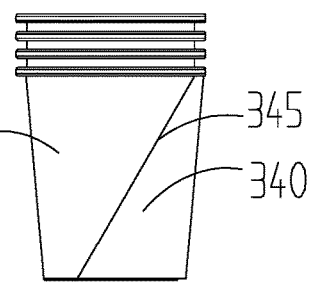
Figure 10A:
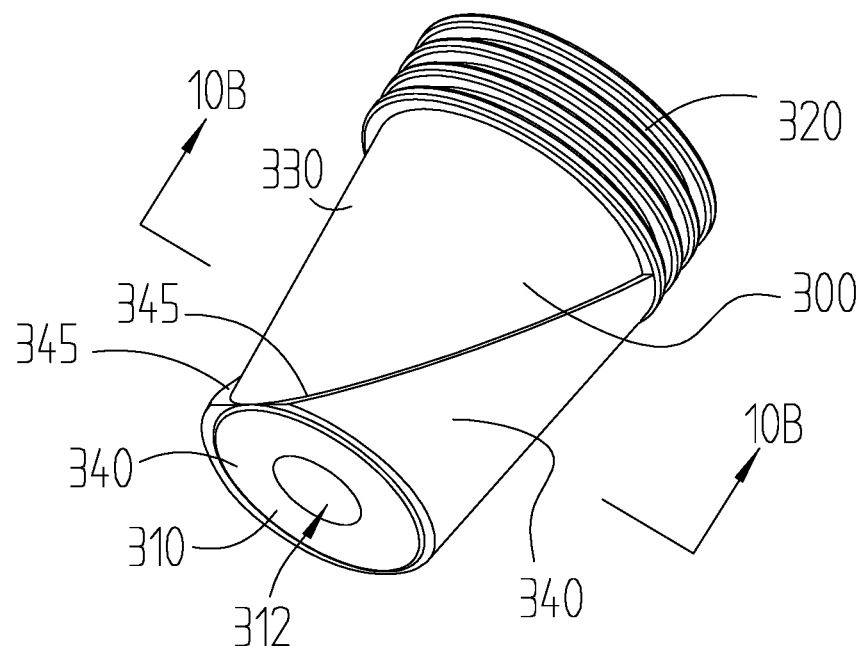
FIG. 10A is a perspective view of a tubular member, illustrative of another embodiment of the present disclosure.
Figure 10B:
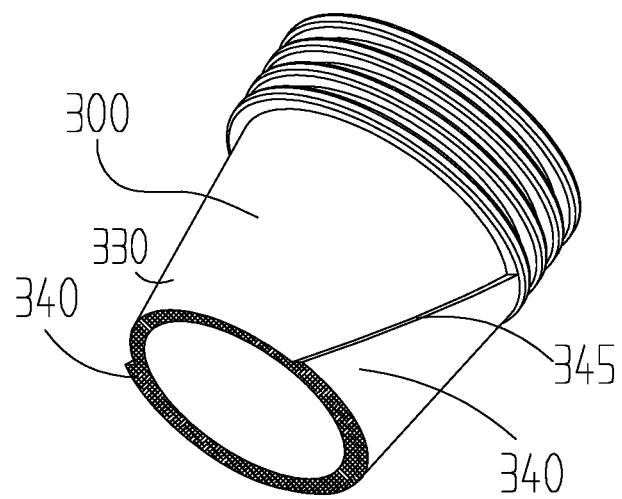
FIG. 10B is a perspective view of a cut-off portion of the tubular member of FIG. 10A, taken along line 10B-10B in FIG. 10A.

FIGS. 9D, 9E and 9F illustrate that a helical ridge 340 may have different widths in different embodiments, and a helical ridge 340 may be positioned at different positions. For example, as shown in FIG. 9D, the helical ridge 340 has a relatively large width and the thinner wall area 332 is much larger in area size than the thinner wall area 334. In FIG. 9E, the middle tubular section 330 of tubular member 300 has only different regions, the thinner wall area 332 and the thicker helical ridge 340 (the area 334 does not exist or has a size of zero), which are separated by the helical boundary 345. In FIG. 9F, the thinner wall area 332 has a larger area size as compared to FIG. 9E, and the helical ridge 340 has a correspondingly smaller area size as compared to FIG. 9E. FIGS. 10A and 10B show perspective views of tubular member 300 shown in FIGS. 9E and 9F respectively.

Figure 9G:
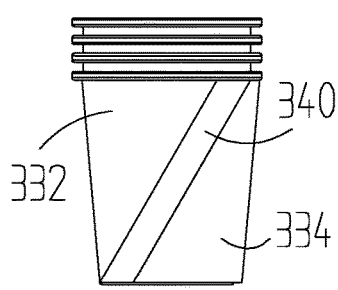
Figure 9H:
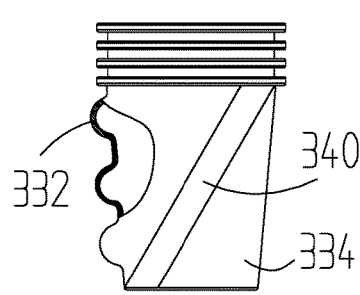
FIGS. 9H and 9I are elevation views with partial sectional views of different tubular members, according to further different embodiments of the present disclosure.
Figure 9I:
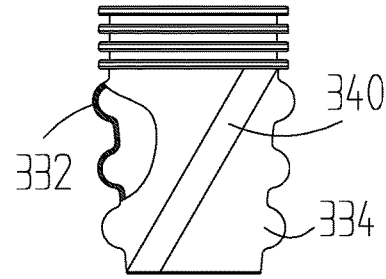

In the embodiment of the tubular member 300 shown in FIG. 9G, the wall 332 and wall 334 have different wall thicknesses. For example, wall 332 may be thinner than wall 334. In this case, when tubular member 300 is stretched, walls 332 and 334 produce different biasing forces, the force produced by wall 334 being larger than that produced by wall 332. Such force differential affects the total lateral biasing force, in addition to the effects produced by the helical ridge 340.

FIG. 9H illustrates an embodiment of the tubular member 300 where the tubular wall 332 in the middle section is corrugated or is a bellows section. Wall 334 in FIG. 9H is not corrugated. FIG. 9I illustrates an embodiment of the tubular member 300 where both the wall 332 and wall 334 are corrugated or bellows sections.

As can be appreciated, when one or more areas of the middle tubular section 330 has curved or corrugated walls, the walls at different areas may have different rectified lengths, which are longer than a straight wall. For a curved line, its rectified length refers to the length of the curve that has been rectified. When rectified, the curve gives a straight line segment with the same length as the curve's arc length. For a straight line, its rectified length is the same as the length of the straight line.

In the embodiment shown in FIG. 9H, wall 334 has a shorter rectified length than wall 332 so that wall 334 would be tensioned more than wall 332 when the middle tubular section 330 is stretched due to downward movement of the needle bundle 200.

As can be appreciated, in the embodiment of FIG. 9H, the corrugated wall 332 is less tensioned than the non-corrugated wall 334 when the tubular member 300 is stretched. Thus, the longitudinal forces produced by walls 332 and 334 are not balanced and the imbalance produces an additional lateral biasing force.

Figure 11A:
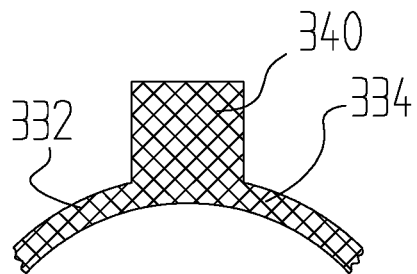
FIG. 11A is a cross-sectional view of the helical ridge of the tubular member of FIG. 7A, taken along line 11A-11A in FIG. 7A.
Figure 11B:
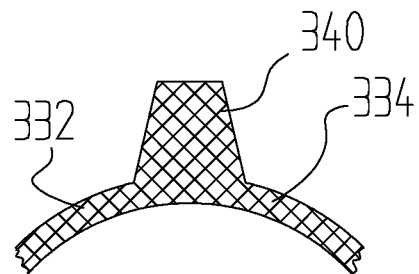
FIGS. 11B to 11F are cross-sectional views of different helical ridges, according to different embodiments of the present disclosure.
Figure 11C:
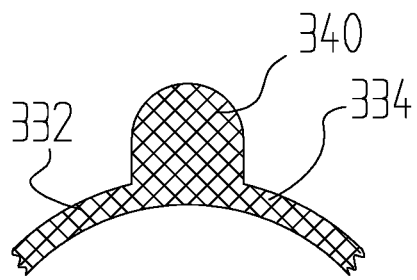
Figure 11D:
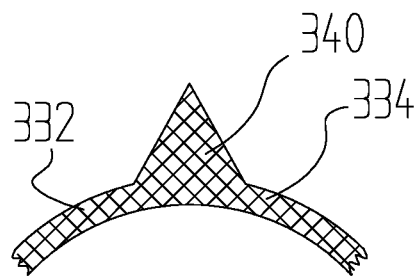
Figure 11E:
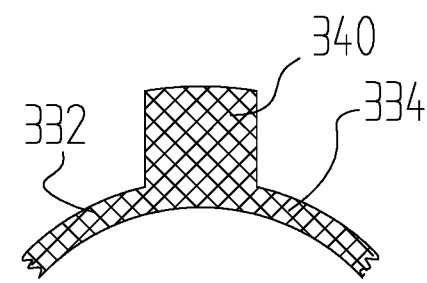
Figure 11F:
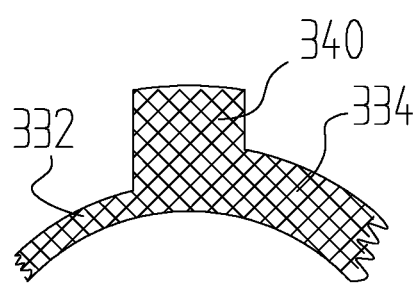

A helical ridge 340 may have any number of cross-sectional shapes or profiles, some of which are illustrated in FIGS. 11A to 11F. For example, the cross-section profile of a helical ridge 340 may be generally polygonal or semicircular. The polygonal cross-section may be square, as illustrated in FIG. 11A; trapezoidal, as illustrated in FIG. 11B; triangular, as illustrated in FIG. 11D; or rectangular, as illustrated in FIGS. 11E and 11F. The cross-section profile of a helical ridge 340 may also include a semicircular edge as illustrated in FIG. 11C.

In FIGS. 11A-11E, wall 332 and wall 334 have the same wall thickness. In FIG. 11F, wall 334 is thicker than wall 332. In any event, the wall thickness at helical ridge 340 is larger than at both walls 332 and 334.

In FIGS. 11E and 11F, the helical ridge 340 has a generally rectangular cross-sectional profile, but the top edge may be curved or arched. For example, the outer top edge of helical ridge 340 may be concentric with the tubular section formed by walls 332 and 334.

Conveniently, the helical ridge 340 or different portions having a helical boundary and different thickness, when stretched, can provide a biasing force that biases the needle bundle both longitudinally towards the retracted position and laterally towards a lateral side of the channel 120.

Tubular member 300 also conveniently provides a fluid seal between the upper open end and lower open end of the housing channel 120.

As compared with the biasing member disclosed in U.S. Ser. No. 11/052,232 or the elastic membrane disclosed in CN 106902452A, a tubular member as described herein provides a number of beneficial effects or advantages.

Figure 7C:
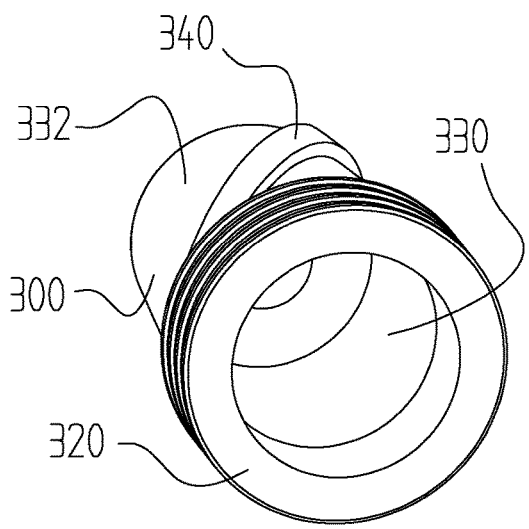
FIG. 7C is a top perspective view of the tubular member of FIG. 7A.
Figure 7D:
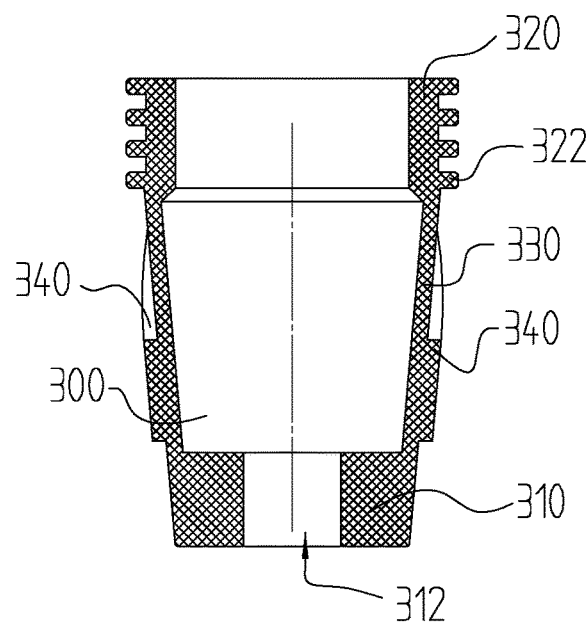
FIG. 7D is a cross-sectional view of the tubular member of FIG. 7A along line 7D-7D in FIG. 7A.

For example, a tubular member with one or more helical ridges as described herein is easier to manufacture, as compared to an elastic tubing with opposite sides of different rectified lengths and corrugated tubular sections. For instance, when manufactured by molding, the internal shapes of the molds for producing the tubular member 300 illustrated in FIGS. 7A, 7C, and 7D are not as complex as in a mold for producing a biasing member with different rectified lengths and corrugated tubular sections. As a result, the production efficiency and product yield can be improved. Further, it is easier to inspect small defects on the external surface of a product with simpler external surface features.

The elastic membrane disclosed in CN 106902452A have regions of different thicknesses and the boundaries between the different regions extend in the axial or longitudinal direction. The elastic membrane of CN 106902452A may have an elastic rib extending along the direction of the needle movement on one side of the elastic membrane. A drawback of the elastic membrane disclosed in CN 106902452A is that it is difficult to adjust amounts, or ratio, of the generated forces in different directions. For example, while the thicknesses of the different portions of the membrane may be adjusted to generate different force ratios, a large thickness difference in the same membrane can result in manufacturing complexity and reduction in performance and product durability.

As compared to a region boundary or elastic rib that extends linearly along the axial or longitudinal direction of the needle, a helical ridge or boundary as described herein can provide additional lateral forces that can be more easily adjusted by changing the helical direction without changing the thickness of the helical ridge or any portion of the tubular membrane. For example, a higher lateral to longitudinal biasing force ratio may be achieved with a helical ridge or boundary without changing the thicknesses of the tubular member.

The needle module 10 may be a single-use disposable module, and can be used directly after opening the needle module packaging without further cleaning, sanitization, or sterilization, and can be disposed after a single use without cleaning or any other treatment.

For clarity, it is noted that "single use" may refer to use of a needle or needle module for one complete operation on a single individual subject. During this operation, different needle modules may be used to apply different ink colors or for different purposes. For example, it may be typical to use two to five different types of needles during a single operation on a subject, depending on the complexity of the design to be applied.

As can be appreciated, the tubular member 300 is configured to provide both a longitudinal biasing force and a lateral or radial biasing force, with the provision of a helical ridge or helical boundary.

As now can be appreciated, during operation, the tubular member 300 also separates the lower open end of body portion 100 from the upper open end of body portion 100, and provides a fluid-tight seal in the channel 120 between the lower end and the upper end of the housing 40 such that bodily fluids exiting from the punctured skin of the subject being treated will be prevented from travelling from the needle tip portion 210 to the upper end of the housing through the inner channel 120. The seal also prevents ink from entering and passing through the upper end of needle housing 40. The seal thus conveniently prevents the subject's bodily fluids and ink from contacting parts of the needle handle (not shown) or tattoo machine (not shown) connected to the needle module 10. Conveniently, the tattoo machine and the needle handle may be reused after each treatment or after changing the needle module, without the need to re-sterilize any part of the tattoo machine. In some cases, the needle handle may also be disposable.

It can now also be appreciated that the above convenient effects can also be achieved with different embodiments or variations of tubular member 300 as depicted in the drawings.

As can be appreciated, a needle module or needle assembly described herein may be used or adapted to apply other types of liquids to skin. For example, the applied liquid may include colored liquids or pigments, or may include a medicinal or therapeutic agent, collagen, or other like or similar substances. The needle assembly may be used in a liquid applicator for applying the selected liquid.

Other features, modifications, and applications of the embodiments described here may be understood by those skilled in the art in view of the disclosure herein.

CONCLUDING REMARKS

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments of the present disclosure are intended to be illustrative only and in no way limiting. The described embodiments are susceptible to many modifications of form, arrangement of parts, details, and order of operation. The invention, rather, is intended to encompass all such modification within its scope, as defined by the claims.

List of references and corresponding elements as shown in the figures:

| Reference | Corresponding element |
| --- | --- |
| 10 | Needle module |
| 40 | Housing |
| 100 | Body portion |
| 110 | Guiding wall |
| 120 | Channel |
| 122 | Upper open end |
| 124 | Lower open end |
| 130 | Coupling rib |
| 150 | (lower end) Opening |
| 200 | Needle Bundle |
| 210 | Needle Tip portion |
| 215 | Connection rod |
| 220 | Needle shaft portion |
| 222 | Bore |
| 230 | Shoulder |
| 232 | Collar |
| 234 | Neck section |
| 300 | Tubular member |
| 310 | Lower end portion |
| 312 | Central opening |
| 320 | Upper end portion |
| 322 | Annular ridges |
| 330 | Middle tubular section |
| 332 | First wall |
| 334 | Second wall |
| 340 | Helical ridge |
| 345 | Boundary |
| 400 | Cap |
| 410 | Tube |
| 420 | Annular rim |
| 430 | (lower) Groove |
| 440 | (upper) Groove |
| 450 | (central) Opening |

What is claimed is:

1. A needle assembly for a liquid applicator, comprising:
a housing comprising a longitudinal channel, the channel comprising an upper open end and a lower open end;
a needle bundle movably mounted in the channel, the needle bundle configured and mounted to be driven by a driving shaft to reciprocatively move between a retracted position and an extended position;
a tubular member comprising a first end attached to the housing and a second end attached to the needle bundle to bias the needle bundle to move longitudinally towards the retracted position, the tubular member being elastic and further comprising a helical ridge extending on an external surface of the tubular member such that the helical ridge provides a biasing force that biases the needle bundle laterally toward a lateral side of the channel,
wherein the helical ridge forms a generally geometric helix or spiral.

2. The needle assembly of claim 1, wherein the first and second ends of the tubular member are sealingly attached to the housing and the needle bundle to prevent fluid communication between the lower open end and the upper open end of the housing.

3. The needle assembly of claim 1, wherein the tubular member comprises a diaphragm.

4. The needle assembly of claim 1, wherein the helical ridge extends from the first end to the second end of the tubular member.

5. The needle assembly of claim 1, wherein the helical ridge comprises two helical ridges arranged symmetrically with respect to a plane passing through a longitudinal axis of the tubular member.

6. The needle assembly of claim 1, wherein the helical ridge comprises helically aligned step-shaped side edges.

7. The needle assembly of claim 1, wherein the helical ridge comprises generally straight side edges.

8. The needle assembly of claim 1, wherein the helical ridge comprises curved side edges.

9. The needle assembly of claim 1, wherein the helical ridge comprises two generally parallel side edges.

10. The needle assembly of claim 1, wherein the helical ridge comprises unparallel side edges.

11. The needle assembly of claim 1, wherein the helical ridge comprises a plurality of helically arranged separate ridge sections.

12. The needle assembly of claim 1, wherein the helical ridge comprises a generally polygonal or semicircular cross-section.

13. The needle assembly of claim 12, wherein the polygonal cross-section is triangular, rectangular, or trapezoidal.

14. The needle assembly of claim 1, wherein the tubular member comprises silicone, latex, or rubber.

15. A needle assembly for a liquid applicator, comprising:
a housing comprising a longitudinal channel, the channel comprising an upper open end and a lower open end;
a needle bundle movably mounted in the channel, the needle bundle configured and mounted to be driven by a driving shaft to reciprocatively move between a retracted position and an extended position;
a tubular member comprising a first end attached to the housing and a second end attached to the needle bundle to bias the needle bundle to move longitudinally towards the retracted position, the tubular member being elastic and comprising a first portion and a second portion thinner than the first portion, the first portion and the second portion immediately adjacent to one another, wherein a boundary between the first portion and the second portion extends helically between the first end and the second end,
wherein the boundary forms a generally geometric helix or spiral.

16. The needle assembly of claim 15, wherein the first and second ends of the tubular member are sealingly attached to the housing and the needle bundle to prevent fluid communication between the lower open end and the upper open end of the housing.

17. The needle assembly of claim 15, wherein the first and second portions of the tubular member are separated by two helical boundaries, arranged symmetrically with respect to a plane passing through a longitudinal axis of the tubular member.

18. The needle assembly of claim 15, wherein the second portion of the tubular member comprises a bellows section.

19. The needle assembly of claim 15, wherein the first portion and the second portion of the tubular member are separated by a helically aligned step-shaped side wall or a curved side wall at the boundary.

20. The needle assembly of claim 15, wherein the tubular member comprises silicone, latex, or rubber.

* * * * *